US00PP37047P2

(12) United States Plant Patent
van Swieten

(10) Patent No.: US PP37,047 P2
(45) Date of Patent: Oct. 21, 2025

(54) ***PHALAENOPSIS* PLANT NAMED 'PHA248938'**

(50) Latin Name: *Phalaenopsis hybrida*
Varietal Denomination: PHA248938

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (BE)

( * ) Notice: Subject to any disclaimer, the term of this patent is extended or adjusted under 35 U.S.C. 154(b) by 0 days.

(21) Appl. No.: 18/769,587

(22) Filed: Jul. 11, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP33,905 P3 * 1/2022 Schoone ..... A01H 6/62
Plt./311

OTHER PUBLICATIONS

CPVO Application Consultation Version 4.23.10, retrieved on Apr. 24, 2025 at https://online.plantvarieties.eu/publicConsultationDetails?registeId=20230884&denomination=pha248938, 2 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA248938', characterized by its upright plant habit; moderately vigorous to vigorous growth habit and moderate growth rate; strong flowering stems; strong leaves; freely flowering habit with typically two inflorescences developing per plant, each inflorescence with numerous flowers; reddish purple-colored flowers with orangish white-colored petal and sepal margins; and good postproduction longevity.

2 Drawing Sheets

Figure 1:
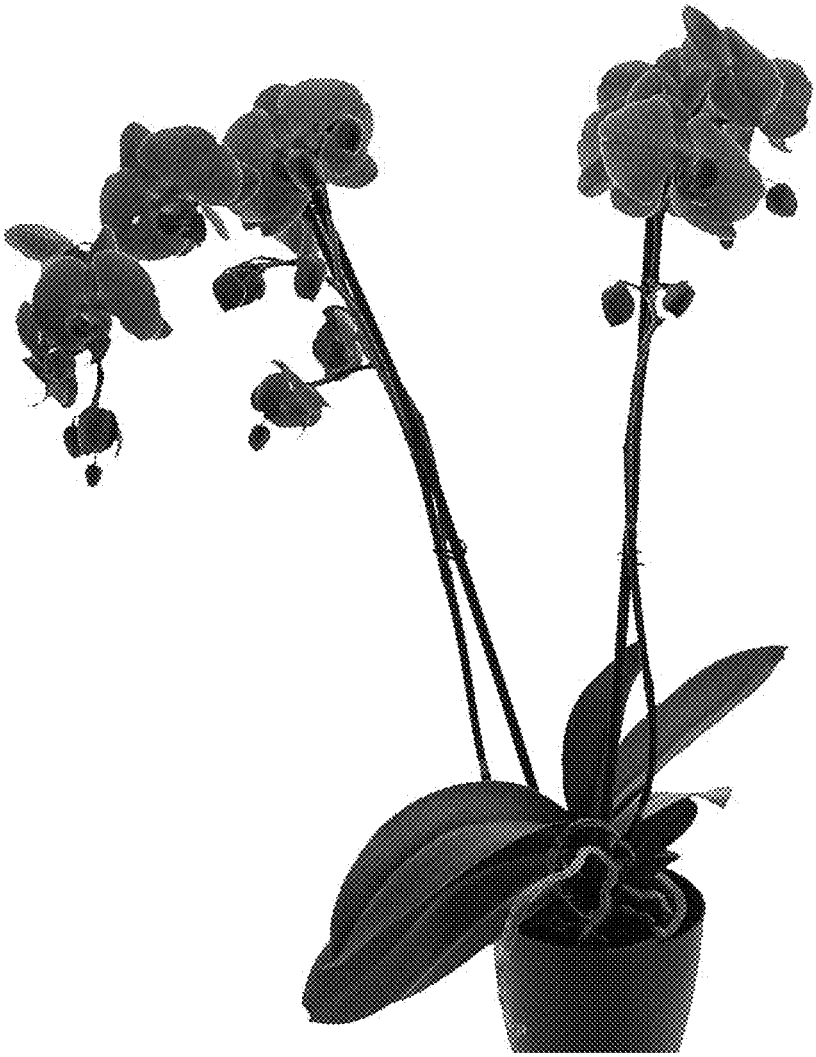

Botanical designation: *Phalaenopsis hybrida.*
Cultivar denomination: 'PHA248938'.

STATEMENT REGARDING PRIOR DISCLOSURES BY INVENTOR and APPLICANT/ASSIGNEE

A European Community Plant Breeder's Rights application for the instant plant was filed by the Applicant/Assignee of the instant application, Anthura B.V. of Bleiswijk, The Netherlands on Apr. 19, 2023, application number 2023/0884. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida,* and hereinafter referred to by the name 'PHA248938'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique and attractive patterns and coloration.

The new *Phalaenopsis* plant originated from a cross-pollination in October 2016 in Bleiswijk, The Netherlands of a proprietary selection of *Phalaenopsis hybrida* identified as code number 00001-4992, not patented, as the female, or seed, parent with a proprietary selection of *Phalaenopsis hybrida* identified as code number 12-52654-01, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in August 2019.

Asexual reproduction of the new *Phalaenopsis* plant by in vitro meristem propagation in a controlled environment in Bleiswijk, The Netherlands since August 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA248938'. These characteristics in combination distinguish 'PHA248938' as a new and distinct *Phalaenopsis* plant:

1. Upright plant habit.
2. Moderately vigorous to vigorous growth habit and moderate growth rate.
3. Strong flowering stems.
4. Strong leaves.
5. Freely flowering habit with typically two inflorescences developing per plant, each inflorescence with numerous flowers.
6. Reddish purple-colored flowers with orangish white-colored petal and sepal margins.
7. Good postproduction longevity.

Plants of the new *Phalaenopsis* can be compared to plants of the female parent selection. Plants of the new *Phalaenopsis* differ primarily from plants of the female parent selection in flower color as plants of the new *Phalaenopsis* are reddish purple in color with orangish white-colored petal and sepal margins whereas plants of the female parent selection have purplish violet-colored flowers.

Plants of the new *Phalaenopsis* can be compared to plants of the male parent selection. Plants of the new *Phalaenopsis* differ primarily from plants of the male parent selection in the following characteristics:

1. Flowers of plants of the new *Phalaenopsis* are not as broad as flowers of plants of the male parent selection.
2. Plants of the new *Phalaenopsis* are reddish purple in color with orangish white-colored petal and sepal margins whereas plants of the male parent selection have light greenish yellow-colored flowers.

Plants of the new *Phalaenopsis* can be compared to plants of *Phalaenopsis hybrida* 'PHALGUIQDI', disclosed in U.S. Plant Pat. No. 32,207. In side-by-side comparisons, plants of the new *Phalaenopsis* differ primarily from plants of 'PHALGUIQDI' in flower color as plants of the new *Phalaenopsis* are reddish purple in color with orangish white-colored petal and sepal margins whereas plants of 'PHALGUIQDI' have purplish-pink striped flowers.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA248938' grown in a container.

Figure 2:
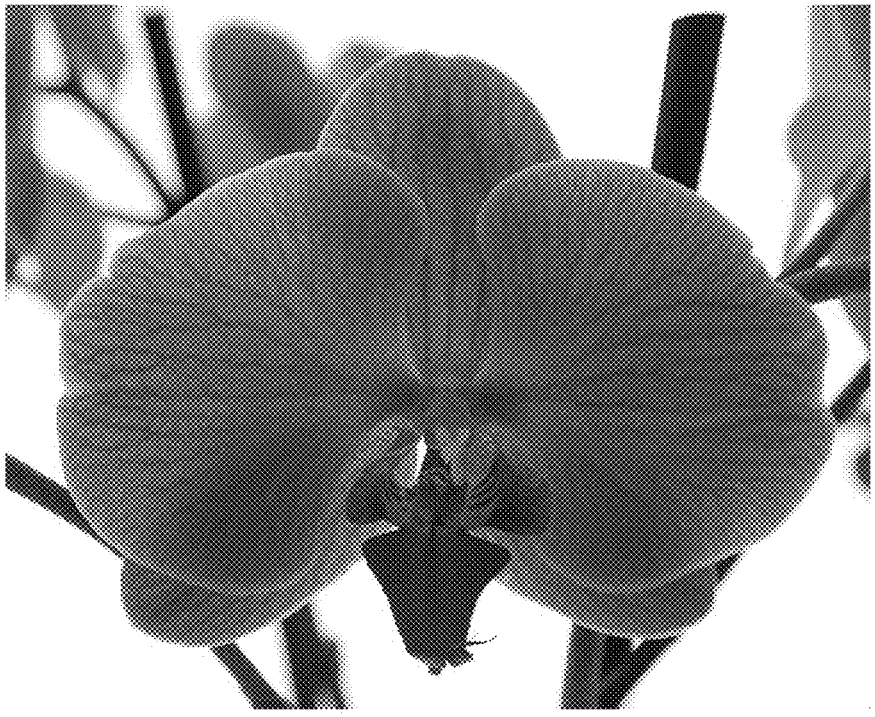

The photograph on the second sheet (FIG. 2) is a close-up view of a typical flower of 'PHA248938'.

DETAILED BOTANICAL DESCRIPTION

The aforementioned photographs and following observations and measurements describe plants grown during the late winter and early spring in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA248938'.

Parentage:

*Female, or seed, parent*.—Proprietary selection of *Phalaenopsis hybrida* identified as code number 00001-4992, not patented.

*Male, or pollen, parent*.—Proprietary selection of *Phalaenopsis hybrida* identified as code number 12-52654-01, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; sparse.

Plant description:

*Plant form and growth habit*.—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane*.—About 13.2 cm.

*Plant height, substrate level to top of floral plane*.—About 51.8 cm.

*Plant diameter or spread*.—About 41.3 cm.

Leaf description:

*Arrangement and quantity*.—Distichous, simple; sessile; about three to four fully-developed leaves per plant.

*Length*.—About 20 cm.

*Width*.—About 7.3 cm.

*Aspect*.—Horizontal to semi-erect.

*Shape*.—Elliptic to oblanceolate; slightly carinate.

*Apex*.—Unequal acute.

*Base*.—Sheathing. Sheath length: About 2.2 cm. Sheath width: About 1.7 cm. Sheath color: Close to 146B moderately to strongly tinged with close to a blend of N186C and 200B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137A; narrow marginal edges, close to 187A and 187B. Developing leaves, lower surface: Close to 146B strongly tinged with close to N186C. Fully expanded leaves, upper surface: Close to NN137B; narrow marginal edges, close to 187A and 187B; venation, close to 139A. Fully expanded leaves, lower surface: Close to 146B; at the margins, strongly tinged with close to N186C; venation, close to 143A and a blend of N186C and 200B.

Inflorescence description:

*Appearance and flowering habit*.—Showy zygomorphic flowers arranged on axillary simple or branched racemes; typically two inflorescences develop per plant; each inflorescence with about 21 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about ten weeks on the plant; flowers not persistent.

*Inflorescence length* (*lowermost flower to inflorescence apex*).—About 46.3 cm.

*Inflorescence width*.—About 30.6 cm.

*Flower buds*.—Height: About 1.9 cm. Diameter: About 1.3 cm by 1.7 cm. Shape: Broadly ovate. Color: Close to 183D and 187D.

*Flower size*.—About 8.5 cm (vertical) by 9.8 cm (horizontal).

*Flower depth*.—About 3.2 cm.

*Petals, quantity and arrangement*.—Three, two lateral petals and one center petal transformed into a labellum.

*Lateral petals*.—Length: About 4.8 cm. Width: About 6.1 cm. Shape: Reniform. Apex: Shallow retuse. Margin: Entire; slightly and coarsely undulate. Texture and luster, upper and lower surfaces: Smooth, glabrous, moderately velvety; matte. Color: When opening, upper surface: Close to a blend of 70B and 186B; towards the base, close to 70A with fine dots, close to 76D; narrow marginal edges, close to 159C; venation, close to 64A. When opening, lower surface: Close to 186C; towards the base, tinged with close to 195B; narrow marginal edges, close to 159C; venation, close to 186A. Fully opened, upper surface: Close to 70B; center, close to 72C; towards the base, close to NN78B with fine dots, close to 76D; narrow marginal edges, close to 159C; venation, close to 71B and 71C; color does not change with subsequent development. Fully opened, lower surface: Close to a blend of 70B and 186C; towards the base, close to 75B, 75C and 76C; narrow marginal edges, close to 159C; venation, close to 70B; color does not change with subsequent development.

*Labella*.—Appearance: Three-parted with two lateral lobes and a central lobe. Length, lateral lobes: About 2.2 cm. Width, lateral lobes: About 1.3 cm. Length, central lobe: About 2.4 cm. Width, central lobe: About 1.8 cm to 2.1 cm. Length, cirrhose tips: About 1.6 cm. Shape, lateral lobes: Obovate. Shape, central lobe: Deltoid to slightly rhomboidal with an elongated apex. Apex, lateral lobes: Obtuse. Apex, central lobe: Acute with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 6 mm in height. Color: When opening, upper surface: Lateral lobes: Lower two thirds, close to 185B; upper third, close to NN78B and at the apex, close to N78D; at the base, close to N155A slightly tinged with close to 4C and 4D with radial stripes, close to 60A. Central lobe: Close to 72A and 72B; towards the base, close to 64A and at the base, close to 75C and N75C with radial stripes, close to 185B; main vein, close to 64A; cirrhose tips, close to 72A and 72B. Callosities: Close to 4D; towards the apex, close to 9B; dense dots and blotches, close to 183A. When opening, lower surface: Lateral lobes: Close to N78B; towards the base, close to 70B and 157C. Central lobe: Close to NN78A; towards the base, close to N77B and at the base, close to 156C, 156D and 60C; central band, close to 186C; cirrhose tips, close to NN78A. Fully opened, upper surface: Lateral lobes: Lower two thirds, close to 185B; upper third, close to NN78B and at the apex, close to N78D; at the base, close to N155A slightly tinged with close to 6B with radial stripes, close to 60A. Central lobe: Close to 72A; center, close to 71A; at the base, close to 155A with radial stripes and blotches, close to 61A and 72A; main vein, close to 71A; cirrhose tips, close to 71A. Callosities: Close to 9D; towards the apex, close to 14A; dense dots and blotches, close to 183A and 183B. Fully opened, lower surface: Lateral lobes: Close to N78B; towards the base, close to 70B and 157C. Central lobe: Close to NN78A; towards the base, close to 70B and at the base, close to 76C and 70A; central band, close to 75A; cirrhose tips, close to N78A.

*Sepals*.—Quantity and arrangement: Three, one upper dorsal sepal and two lower lateral sepals. Length, dorsal sepal: About 4.9 cm. Width, dorsal sepal: About 3.9 cm. Length, lateral sepals: About 4.8 cm. Width, lateral sepals: About 3.3 cm. Shape, dorsal sepal: Broadly elliptic. Shape, lateral sepals: Broadly ovate. Apex, dorsal sepal: Shallow and minutely emarginate. Apex, lateral sepals: Broadly and bluntly acute. Base, dorsal and lateral sepals: Truncate. Margins, dorsal sepal: Entire; not undulate. Margins, lateral sepals: Entire; slightly and coarsely undulate. Texture and luster, dorsal and lateral sepals, upper and lower surfaces: Smooth, glabrous, moderately velvety; matte. Color, dorsal sepal: When opening, upper surface: Close to 186A; towards the margins, apex and base, close to 186B and a blend of 186A and 186B; towards the base, sparse fine dots, close to 76D; narrow marginal edges, close to 159C; venation, close to 64A and 64B. When opening, lower surface: Close to 183D; towards the margins and apex, close to 185C and 185D; narrow marginal edges, close to 159C. Fully opened, upper surface: Close to 63B and 64B; towards the margins and apex, close to 72C and 72D; towards the base, close to NN78C and NN78D with fine dots, close to 76D; narrow marginal edges, close to 159C; venation, close to 71A and 71B. Fully opened, lower surface: Close to 64B; towards the margins and apex, close to 70B, N74C and N74D; at the base, close to N78B; narrow marginal edges, close to 159C; venation, close to N77B. Color, lateral sepals: When opening, upper surface: Close to 186B; towards the apex, close to a blend of 60C and 186A; towards the base, close to 195B and at the base, fine dots, close to 184B and 184C; narrow marginal edges, close to 159C; venation, close to 64A and 64B. When opening, lower surface: Close to 183D; venation, close to 185B. Fully opened, upper surface: Close to 70B; towards the base, close to 75A with fine dots, close to 72A; narrow marginal edges, close to 159C; venation, proximally, close to NN78B and distally, close to 71A and 71B. Fully opened, lower surface: Close to 70B; narrow marginal edges, close to 159C; venation, close to 71A and 71B.

*Peduncles*.—Length: About 63 cm. Diameter: About 6 mm. Strength: Strong. Aspect: Upright to outwardly arching. Texture and luster: Smooth, glabrous; matte. Color: Close to N200A; heavily dotted with fine dots, close to 147B.

*Pedicels*.—Length: About 4.1 cm. Diameter: About 3 mm. Strength: Moderately strong. Aspect: About 35° from peduncle axis. Texture and luster: Smooth, glabrous; matte. Color: Close to 185C and 185D; proximally, close to 187B and distally, close to 75A and 75B.

*Reproductive organs*.—Androecium: Column length: About 9 mm. Column width: About 6 mm. Column color: Close to NN78A and N78B. Pollinia quantity: Two. Pollinia diameter (per two pollinia): About 2.5 mm. Pollinia color: Close to 24A. Gynoecium: Stigma length: About 4 mm. Stigma width: About 4.5 mm. Stigma shape: Reniform. Stigma color: Close to N155A. Ovary length: About 7 mm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis*plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA248938' as herein illustrated and described.

* * * * *